United States Patent [19]

Min-Jenn

[11] Patent Number: 4,975,587

[45] Date of Patent: * Dec. 4, 1990

[54] CONTAINER FOR STORING AND STERILIZING A CHOPPING BOARD

[76] Inventor: Liaw Min-Jenn, 9F., No. 1291, Chern Der Rd., Taipei City, Taiwan

[*] Notice: The portion of the term of this patent subsequent to Oct. 31, 2006 has been disclaimed.

[21] Appl. No.: 387,809

[22] Filed: Aug. 1, 1989

[30] Foreign Application Priority Data

Jul. 4, 1988 [CN] China .......................... 76206510A02
Jun. 17, 1989 [CN] China .......................... 76206510A03

[51] Int. Cl.$^5$ ............................................... A61L 3/00
[52] U.S. Cl. ..................................... 250/455.1; 422/24
[58] Field of Search ......................... 250/455.1; 422/24

[56] References Cited

U.S. PATENT DOCUMENTS 2,245,762 6/1941 Stefani et al. ..................... 250/455.1
3,683,638 8/1972 Devon ................................... 422/24
4,877,963 10/1989 Min-Jenn .......................... 250/455.1

Primary Examiner—Jack I. Berman
Attorney, Agent, or Firm—Bacon & Thomas

[57] ABSTRACT

The present invention relates to a container for storing and sterilizing a chopping board which mainly comprises a case, a scattering plate, a sterilizing lamp, a screen cover, a water collecting box, a supporting plate, a microswitch, a compression spring, a holding plate, a heating element and a bottom plate. The weight of the chopping board forces the supporting plate to contact the microswitch which in turn actuates both the sterilizing lamp and the heating element such that the ultraviolet light generated by the lamp together with the heat produced by the heating element can be scattered by the scattering plate to improve both sterilizing and drying efficacy. In addition, the present container has a compact overall volume and can be easily assembled because the utilized elements are simplified and the number of elements are significantly reduced.

11 Claims, 7 Drawing Sheets

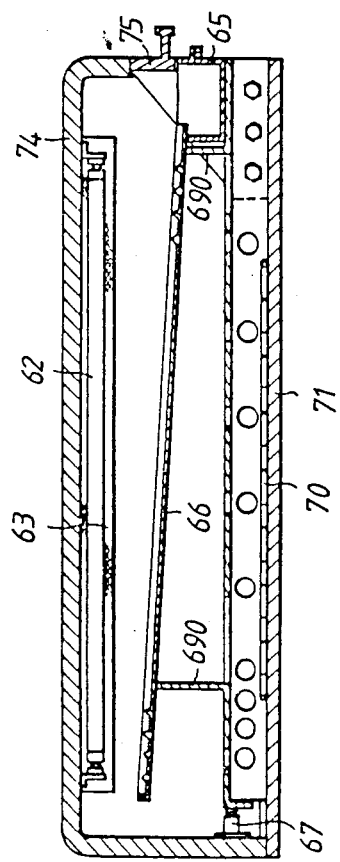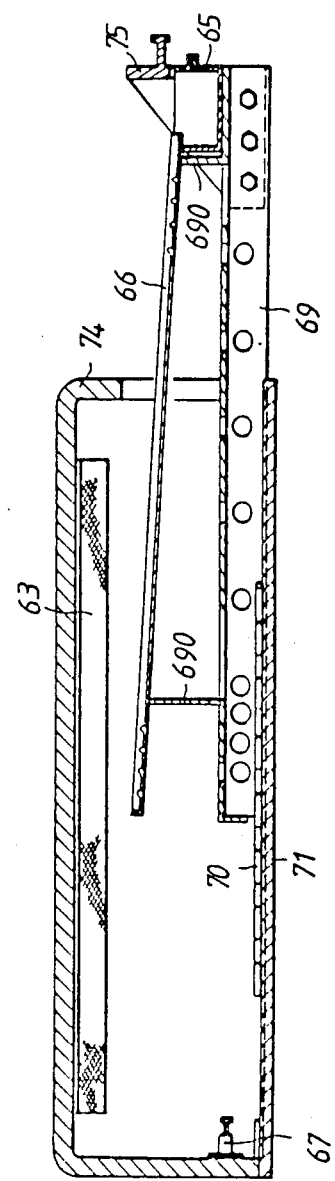

CONTAINER FOR STORING AND STERILIZING A CHOPPING BOARD

BACKGROUND OF THE INVENTION

The present invention relates to a container and particularly to one which is used to store and sterilize a chopping board.

The sanitary requirements for the appliances to be used in the kitchen are increasing day by day. Although many newly designed devices, such as rice container, dish dryer, etc. have already been provided for such purposes, to date we still lack a proper container to store and to sterilize the chopping board which, otherwise, may easily be polluted.

It is, therefore, an object of the present invention to obviate and mitigate the above-identified deficency.

SUMMARY OF THE INVENTION

It is an object of the present invention to provide a container for storing and sterilizing a chopping board which has a simplified structure with a compact volume and is easy to be assembled.

It is another object of the present invention to provide a container for storing and sterilizing a chopping board which comprises a scattering plate by which the ultraviolet light generated by a sterilizing lamp as well as the heat produced by a heating element can be uniformly scattered so as to improve both sterilizing and drying efficacy.

It is another object of the present invention to provide a container for storing and sterilizing a chopping board which can uniformly distribute the heat produced by the heating element to provide a better drying effect.

BRIEF DESCRIPTION OF THE DRAWINGS

FIG. 5 is a perspective view of a fourth preferred embodiment of the present invention;

DETAILED DESCRIPTION OF THE PREFERRED EMBODIMENTS

Figure 1:
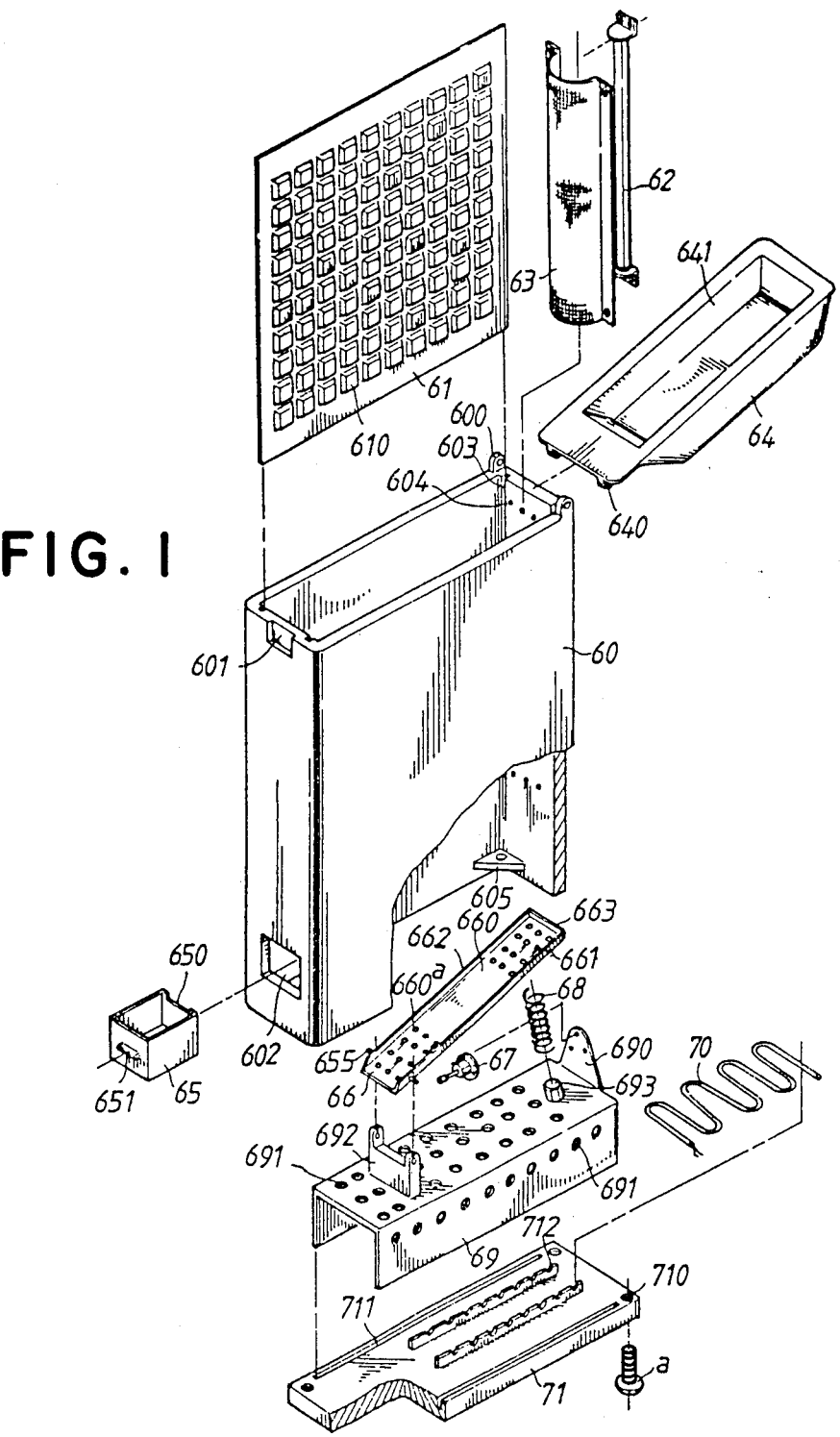
FIG. 1 is a fragmentary view of a first preferred embodiment of the present invention.

Referring to FIG. 1, a first preferred embodiment of the present invention mainly comprises a rectangular hollow case 60, one or more scattering plates 61, one or more sterilizing lamps 62, a screen cover 63, an upper cover 64, a water collecting box 65, a supporting plate 66, a microswitch 67, a compression spring 68, a holding plate 69, a heating element 70 and a bottom plate 71. The rectangular hollow case 60 is formed at the upper portion of one of longitudinal side wall with a pair of ears 600 to which the upper cover 64 is hinged and at the other longitudinal side wall with a recessed portion 601 to facilitate the opening of the upper cover 64. The case 60 further is provided at the bottom with an opening 602 through which the water collecting box 65 can pass to be disposed in the case 60. The inner walls of the case 60 are furnished with slots 603 for engaging with the scattering plates 61 and with a plurality of threaded holes 604 for locating the sterilizing lamps 62 and the screen cover 63. The four lower corners of the case 60 are properly formed with four fixing pieces 605 by which the bottom plate 71 is threadedly secured to the case 60. The scattering plate 61 is made by punching its smooth surface to form a plurality of projecting portions 610 in order to serve as a reflective plate. The upper cover 64 is provided with a pair of flanges 640 corresponding to the ears 600 of the case 60, and with a centrally located recess 641. The water collecting box 65 has a recessed portion 650 through which the open end of the supporting plate 66 passes, and a knob 651 by which the water collecting box 65 can be easily drawn out of the case 60. The supporting plate 66 comprises a plate surface 660 having a plurality of protuberances 600a, three side walls 661, 662 and 663 respectively surrounding its three sides and projecting upward from the plate surface, a projecting rod 664 formed on the underside of the plate surface 660 to be engaged with one end of the compression spring 68, and a pair of pins 665 disposed at two longitudinal sides 661 and 662 thereof. The holding plate 69 has an inverted U-shaped body having a plurality of holes 691 and is formed with a connection member 690 to which the microswitch 67 is secured. The upper surface of the holding plate 69 is properly formed with a fixing seat 692 by which the supporting plate 66 is supported and an inclined stud 693 for engaging with the other end of the compression spring 68. The heating element 70 is an S-shaped, or the like, heating tube. The bottom plate 71 is designed to be disposed in the hollow interior of the case 60. The four corners of the bottom plate 71 have four through holes 710. The bottom plate 71 is provided along its two sides within a pair of grooves 711 with which the holding plate 69 is engaged, and at the center with two parallel rails 712 on which the heating element 70 is located.

Figure 2:
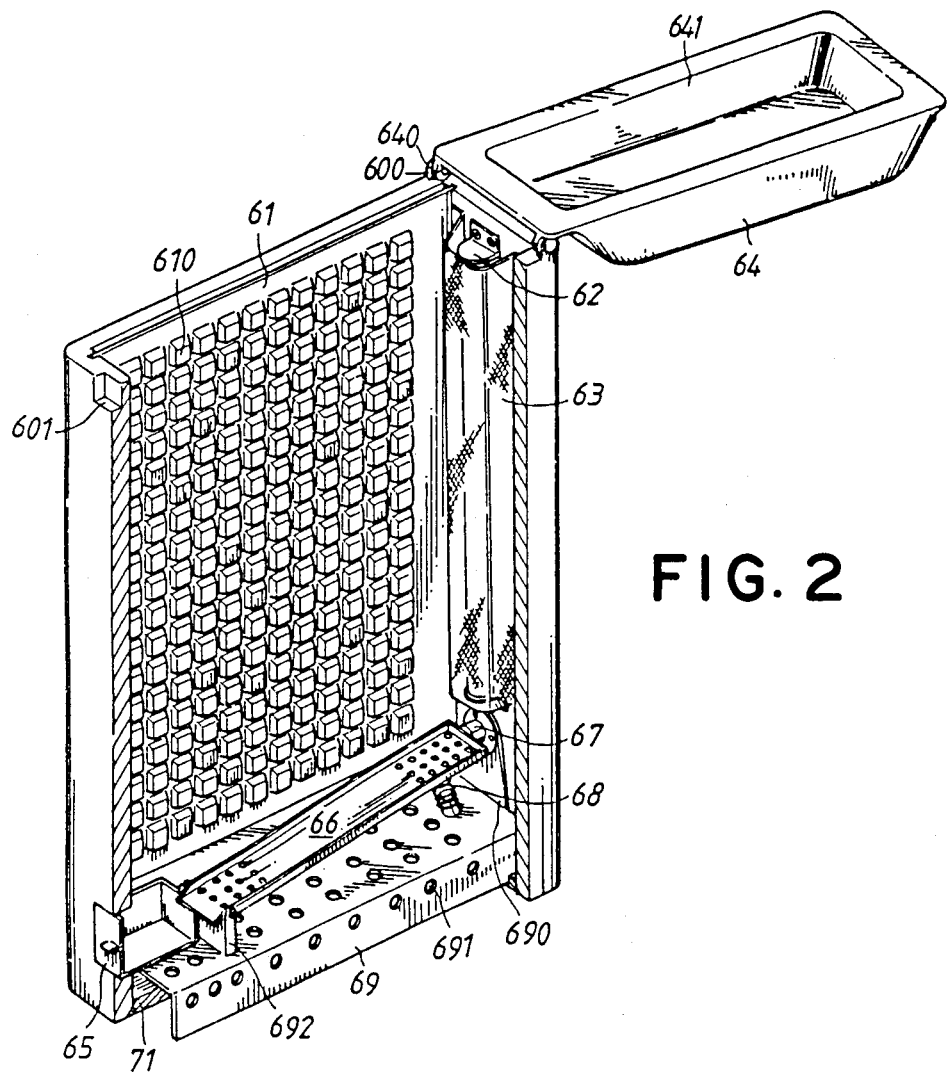
FIG. 2 is a cut-away view of the first preferred embodiment as shown in FIG. 1.

Referring to FIG. 2, in assembly, the sterilizing lamp 62 together with the screen cover 63 are secured to the threaded holes 604 of the case 60 by means of screws or the like. Then, the microswitch 67 is fixed to the connection member 690 of the holding plate 69. One end of the compression spring 68 is connected to the projecting rod 664 on the underside of the plate surface 660 of the supporting plate 66 and the other end thereof is fixed to the inclined stud 693 of the holding plate 69 such that the pins 665 of the supporting plate 66 are engaged with slots of the fixing seat 692 to make the supporting plate 66 incline toward the water collecting box 65. The parallel rails 712 of the bottom plate 71 are used to support the heating element 70 while the grooves 711 therein are used to secure the holding plate 69. The bottom plate 71 is fixed to the fixing pieces 605 of the case 60 by screws (a) to enclose the supporting plate 66 and the holding plate 69 in the interior of the case 60. Then, the scattering plate 61 is engaged with the slots 603 of the case 60. Finally, the upper cover 64 is pivotally connected to the case 60 by engaging the flanges 640 with the corresponding ears 600.

In addition, a cleaned shopping board is placed on the plate surface 660 of the supporting plate 66 whereby the protuberances 660a on the plate surface 660 may form a space between the chopping board and the plate surface 660 such that the water coming from the wet chopping board may drop onto the plate surface 660 and then flow into the water collecting box 65 disposed at the outlet of the supporting plate 66. Meanwhile, the weight of the chopping board forces the supporting plate 66 downward to contact the microswitch 67 which in turn actuates the sterilizing lamp 62 and the heating element 70 to generate the ultraviolet light and the heat, respectively. The scattering plate 61 is used to scatter the ultraviolet light generated by the sterilizing lamp and the heat produced by the heating element 70 to the whole interior of the case 60. The finished container can be attached to any desired location by means of conventional adhesive means because it has a compact volume resulting from the simplified elements and the reduced number of same.

Figure 3:
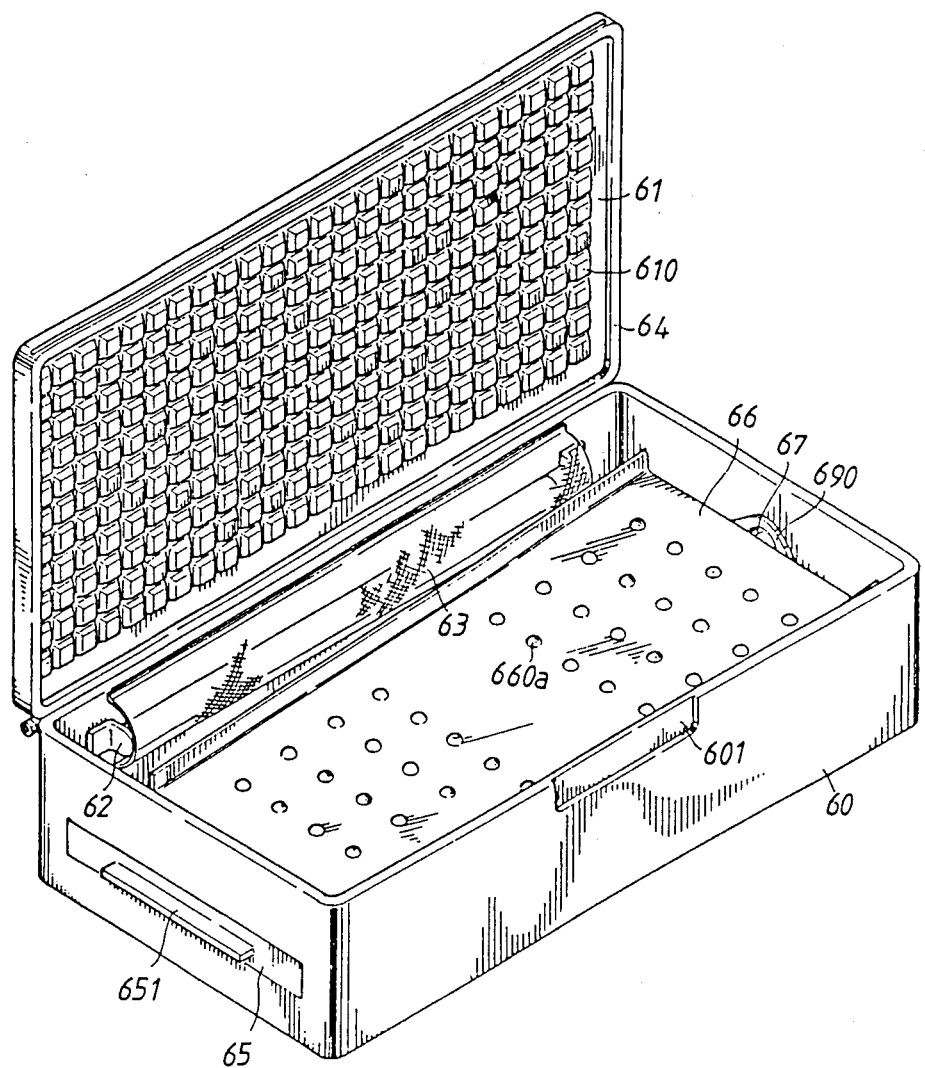
FIG. 3 is a perspective view of a second preferred embodiment of the present invention.

Referring to FIG. 3, a second preferred embodiment of the present invention comprises a case 60 in which a sterilizing lamp 62, a screen cover 63, a water collecting box 65, a supporting plate 66, a compression spring 68, a holding plate 69, a heating element 70 and a bottom plate 71 are received. The above-identified components are substantially similar to those as shown in FIG. 1 and FIG. 2 except that the diamensions of them have been modified in accordance with the case 60. It is to be noted that a scattering plate 61 is disposed in an upper cover 64 which is hinged to the longitudinal edge of the case 60. In operation, the chopping board is placed on the supporting plate 66 such that the weight of the chopping board forces the supporting plate 66 downward to contact the microswitch 67 in order to actuate the sterilizing lamp 62 and the heating element 70 whereby the ultraviolet light generated by the sterilizing lamp together with the heat produced by the heating element 70 are uniformly distributed by the scattering plate 61 to achieve both sterilizing and drying efficacy.

Figure 4:
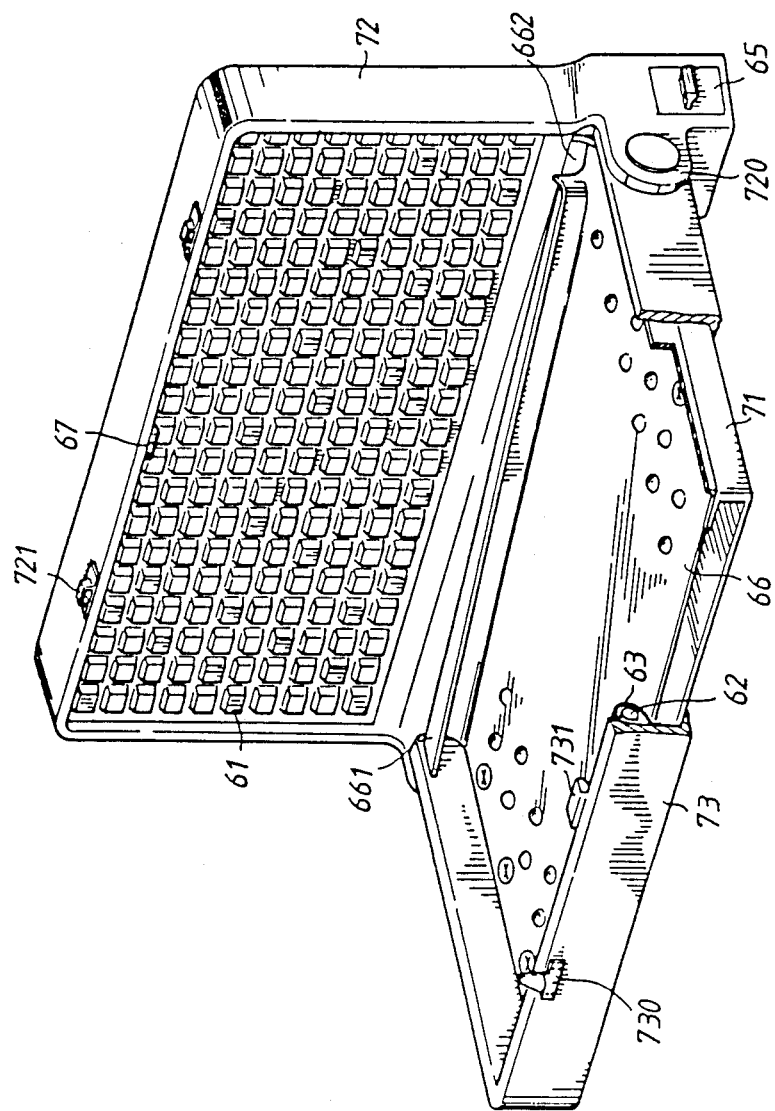
FIG. 4 is a perspective view of a third preferred embodiment of the present invention.

Referring to FIG. 4, a third preferred embodiment of the present invention mainly comprises a fixed case 72 and a moveable case 73 pivotally connected to the fixed case 72. A bottom plate 71, a heating element 70, a supporting plate 66, a sterilizing lamp 62 and a screen cover 63 are all disposed in the moveable case 73 wherein the supporting plate 66 together with the bottom plate 71 are secured to the moveable case 73. The supporting plate 66 has a plurality of protuberances 660a on the surface thereof and is provided with a slot 661 which is arranged to be inclined toward a water collecting box 65 and with an outlet 662. The heating element 70 is received in the bottom plate 71. In assembly, the fixed case 72 may be properly mounted to the wall of the kitchen and then the moveable case 73 is hinged to the fixed case 72. In operation, firstly, the cleaned chopping board is placed on the supporting plate 66 and then the fixed case 72 is covered with the moveable case 73 by inserting each male fastener 730 of the moveable case 73 into the corresponding female fastener 721 of the fixed case 73 in order to enclose the chopping board therein. Then, the chopping board slides into the slot 661 of the supporting plate 66 and is inclined toward the outlet 662 such that the water coming from the wet chopping board may flow into the water collecting box 65 via the slot 661. Meanwhile, a projecting block 731 of the moveable case 73 contacts the microswitch 67 formed in the inner wall of the fixed case 72 to actuate the sterilizing lamp 62 and the heating element 70 for achieving both sterilizing and drying effect when the male fasteners 730 are engaged with the female fasteners 721. Referring to FIG. 5, a fourth preferred embodiment of the present invention mainly comprises a drawer type case 74, a supporting plate 66, a holding plate 69, a microswitch 67, a water collecting box 65, a knob 75, a sterilizing lamp 62, a screen cover 63, a heating element 70 and a bottom plate 71. The sterilizing lamp 62, the screen cover 63 and the scattering plate 61 are properly disposed in the case 74 while the bottom plate 71 is secured to the bottom of the case 74. The heating element 70 is properly located on the surface of the bottom plate 71. The holding plate 69 is slidably disposed in the case 74. The holding plate 69 is provided at the front end with a knob 75 and at the upper surface with a pair of supporting members 690 whereby the outlet of the supporting plate 66 is arranged to correspond to the water collecting box 65.

In operation, firstly, the holding plate 69 is drawn out of the case 74. Then, the holding plate 69 is pushed into the case 60 after the cleaned chopping board has been placed on the supporting plate 66. After the holding plate 69 is received in the case 74, the rear end of the holding plate 69 contacts the microswitch 67 formed on the inner wall of the case 74 to actuate the sterilizing lamp 62 and the heating element 70 whereby the ultraviolet light generated by the sterilizing lamp 62 and the heat produced by the heating element 70 can be uniformly distributed within the interior of the case 74 to achieve both sterilizing and drying effects.

Figure 6:
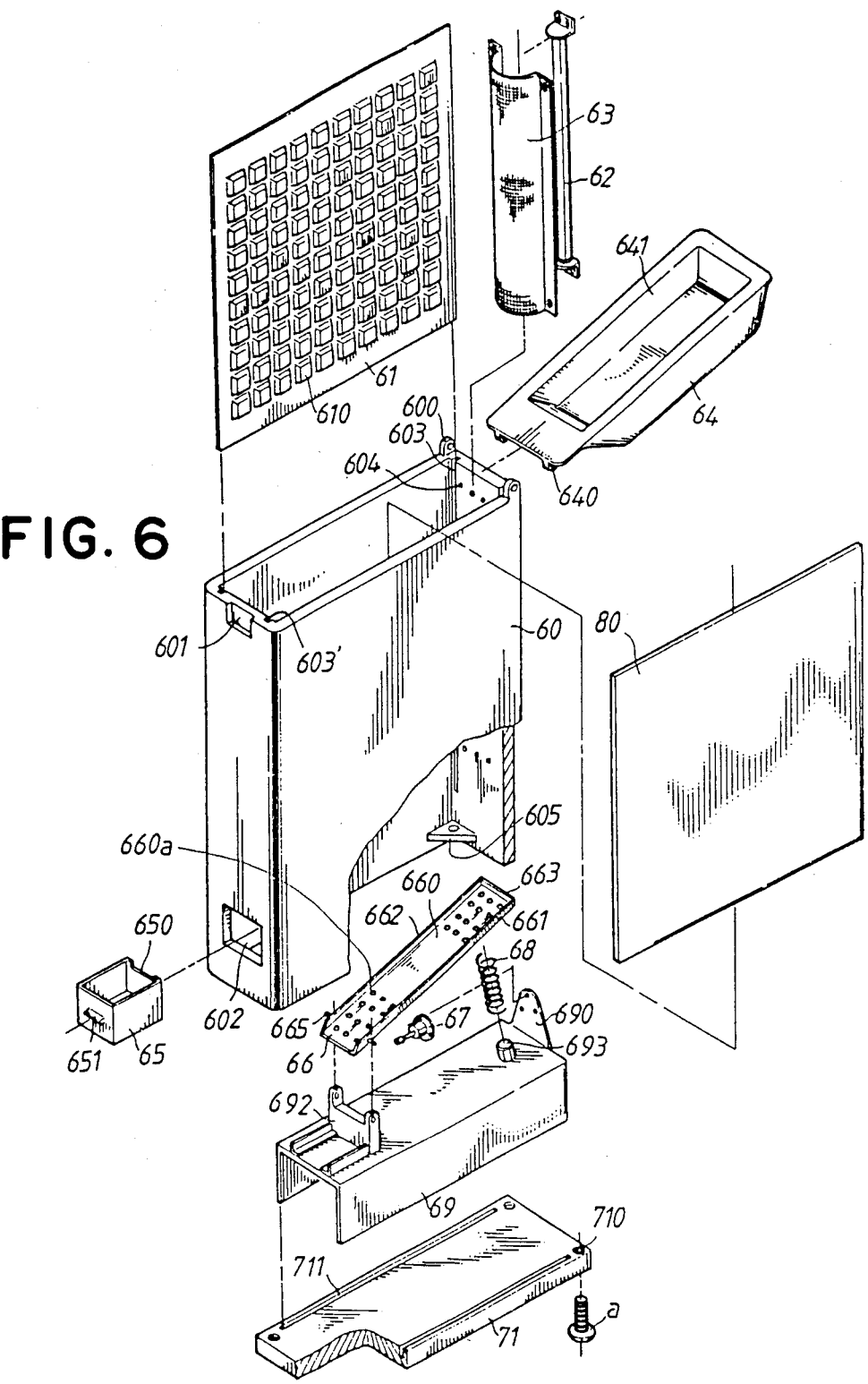
FIG. 6 is a fragmentary view of a fifth preferred embodiment of the present invention.
Figure 7:
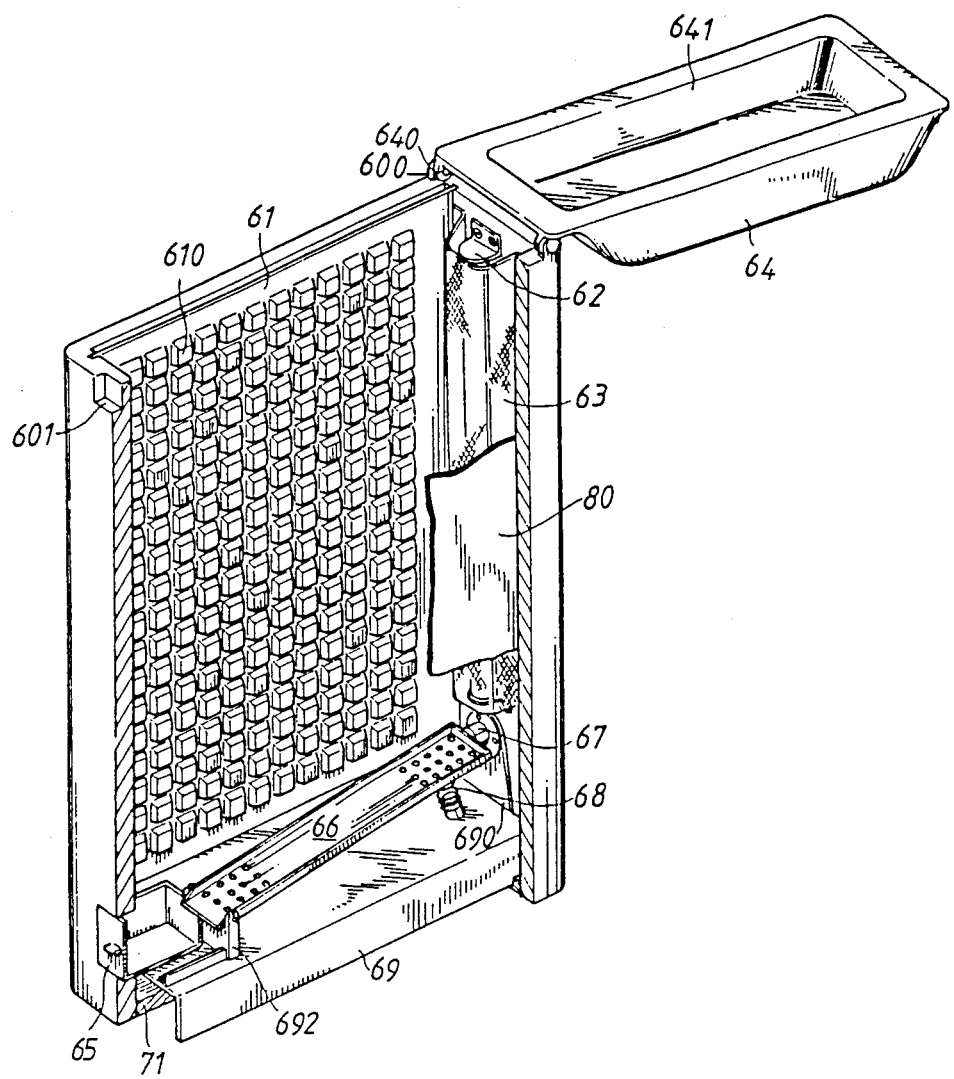
FIG. 7 is a cut-away view of the fifth preferred embodiment as shown in FIG. 6.

Referring to FIGS. 6 and 7, a square plate 80 made of ceramic material is used to substitute for the conventional heating element. The case 60 is provided at its inner wall with a pair of grooves 603 to locate the ceramic plate 80 which is opposite to the scatering plate 61. Alternatively, the ceramic material may be directly located on the inner wall of the case 60 to form a heating layer. As is commonly known, the ceramic material can be processed to have semiconductor characteristics by utilizing the process of doping or nonstoichiometry. These ceramic material having such semiconductor characteristics can meet requirements for various applicaions. For instance, a doped SiC can be processed to become a high temperature, stable semiconductor material to serve as a resistive heating element. In this way, the temperature up to at least 100° C. can be reached under any kinds of operating conditions by merely controlling the resistivity as well as the cross sectional area of the SiC.

I claim:

1. A container for storing and sterilizing a chopping board comprising:
  (a) a rectangular case provided with an access opening, a cover for closing off the access opening, the case and cover collectively defining an internal compartment for receiving a chopping board therein;
  (b) at least one sterilizing lamp disposed within the internal compartment and a screen cover surrounding the lamp;
  (c) a heating element disposed within the internal compartment;
  (d) a bottom plate supported adjacent a lower portion of the internal compartment;
  (e) a holding plate mounted on the bottom plate;
  (f) an inclined supporting plate mounted on the holding plate, the supporting plate including a surface provided with a plurality of protuberances for engagement by the chopping board;
  (g) a microswitch for activation in response to engagement of the supporting plate by the chopping board for operating the sterilizing lamp and heating element;

(h) at least one scattering plate provided with a plurality of geometric protuberances thereon disposed within the internal compartment for scattering sterilizing light and heat generated by the sterilizing lamp and heating element to sterilize and dry the chopping board; and (i) a box disposable adjacent the lower portion of the inclined supporting plate for collecting water from the chopping board.

2. The container of claim 1 wherein:

(a) the cover is hinged to the case;

(b) the case includes a pair of opposed longitudinal side walls, each side wall being provided with a first slot formed along its internal surface; and (c) the scattering plate includes a pair of opposed edges engageable within the first slots.

3. The container of claim 2 wherein:

(a) each side wall is provided with a second slot formed in its internal surface; and (b) the heating element includes a ceramic plate having a pair of opposed edges engaged within the second slots.

4. The container of claim 1 wherein:

(a) the cover is hinged to a longitudinal edge of the case; and (b) the scattering plate is supported on an inner surface of the cover.

5. The container of claim 1 further including:

(a) a pair of parallel rails on the bottom plate, each rail including an upper edge provided with a plurality of grooves; and (b) the heating element is supported within the grooves of the rails.

6. The container of claim 1 further including:

(a) a compression spring;

(b) the lower portion of the supporting plate is pivotally mounted to the holding plate; and (c) the supporting plate is maintained in an inclined position by the compression spring.

7. The container of claim 1 wherein:

(a) the internal corners of the case are provided with connection means;

(b) the bottom plate is secured to the connection means and includes a pair of parallel grooves formed in an upper surface thereof; and (c) the holding plate is of a U-shaped configuration and includes a pair of downwardly directed edges disposed within the grooves.

8. The container of claim 1 wherein the holding plate is of a substantially U-shaped configuration and includes a plurality of apertures formed therein.

9. The container of claim 1 wherein:

(a) the inclined supporting plate is defined by a pair of longitudinal side edges, a bottom edge at the lower portion of the plate and a top edge at the upper portion of the plate; and (b) a side wall extending upwardly from each of the two longitudinal and top edges of the plate.

10. A container for storing and sterilizing a chopping board comprising:

(a) a stationary case and a moveable case, the moveable case being pivotally secured to the stationary case for pivotal movement between open and closed positions;

(b) a bottom plate disposed within the moveable case;

(c) a supporting plate mounted on the bottom plate and including a plurality of protuberances for engagement by a chopping board, the supporting plate including a slot formed along an edge thereof, the slot being inclined when the moveable case is in the closed position for engagement by the chopping board and draining water therefrom downwardly along the slot;

(d) a water box disposed adjacent the lower portion of the inclined slot for collecting water from the chopping board;

(e) a projecting block carried by the moveable case and a microswitch carried by the stationary case for activation by the projecting block when the moveable case is disposed in the closed position to operate a sterilizing lamp and heating element;

(f) a scattering plate provided with a plurality of geometric protuberances formed thereon disposed within the stationary case for scattering sterilizing light and heat generated by the sterilizing lamp and the heating element to sterilize and dry the chopping board; and (g) cooperating fastening means carried by the moveable and stationary cases for maintaining the moveable case in the closed position.

11. A container for storing and sterilizing a chopping board comprising:

(a) a rectangular case including a top wall, a bottom wall, a back wall and a front wall partly defining an internal compartment, the front wall being provided with an access opening;

(b) a bottom plate secured to an inner surface of the bottom wall;

(c) a heating element supported on the bottom plate;

(d) a holding plate provided with a plurality of apertures therein and slidably receivable within the internal compartment through the access opening;

(e) a supporting plate mounted on the holding plate, the supporting plate being inclined from the back wall towards the front wall and including a plurality of protuberances on an upper surface thereof for engagement by the chopping board;

(f) a water box positioned adjacent the lower portion of the inclined supporting plate for collecting water from the chopping board;

(g) a sterilizing lamp mounted on an internal surface of the upper wall and a screen cover surrounding the lamp; and (h) a microswitch activated in response to disposition of the holding plate within the internal compartment for operating the heating element and sterilizing lamp to dry and sterilize the chopping board.

* * * * *